United States Patent
Shin et al.

(10) Patent No.: US 10,646,857 B2
(45) Date of Patent: May 12, 2020

(54) CATALYST SYSTEM FOR OLEFIN OLIGOMERIZATION AND METHOD FOR OLIGOMERIZING OLEFINS USING THE SAME

(71) Applicant: LOTTE CHEMICAL CORPORATION, Seoul (KR)

(72) Inventors: Min Jae Shin, Daejeon (KR); Tae-Jin Kim, Sejong-si (KR); Seung Woong Yoon, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 0 days.

(21) Appl. No.: 15/751,938

(22) PCT Filed: Sep. 21, 2016

(86) PCT No.: PCT/KR2016/010526
§ 371 (c)(1),
(2) Date: Feb. 12, 2018

(87) PCT Pub. No.: WO2017/052187
PCT Pub. Date: Mar. 30, 2017

(65) Prior Publication Data
US 2018/0229226 A1 Aug. 16, 2018

(30) Foreign Application Priority Data
Sep. 23, 2015 (KR) .................. 10-2015-0134727

(51) Int. Cl.
| | | |
|---|---|---|
| *B01J 31/18* | (2006.01) | |
| *C08F 4/69* | (2006.01) | |
| *B01J 31/24* | (2006.01) | |
| *B01J 31/14* | (2006.01) | |
| *C07C 2/32* | (2006.01) | |

(52) U.S. Cl.
CPC .......... *B01J 31/181* (2013.01); *B01J 31/143* (2013.01); *B01J 31/18* (2013.01); *B01J 31/24* (2013.01); *C07C 2/32* (2013.01); *C08F 4/69* (2013.01); *B01J 2231/20* (2013.01); *B01J 2531/62* (2013.01); *C07C 2531/14* (2013.01); *C07C 2531/18* (2013.01); *C07C 2531/22* (2013.01)

(58) Field of Classification Search
CPC combination set(s) only.
See application file for complete search history.

(56) References Cited

U.S. PATENT DOCUMENTS

| | | | |
|---|---|---|---|
| 3,884,833 A | 5/1975 | Wilke et al. | |
| 4,163,024 A | 7/1979 | Heimbach et al. | |
| 6,034,240 A * | 3/2000 | La Pointe | B01J 31/143 546/24 |
| 7,361,623 B2 | 4/2008 | Dixon et al. | |
| 2002/0035029 A1* | 3/2002 | Yoshida | B01J 31/0231 502/154 |
| 2006/0229480 A1* | 10/2006 | Blann | B01J 31/14 585/535 |
| 2015/0065669 A1* | 3/2015 | Hlavinka | C08F 4/65904 526/160 |
| 2015/0148502 A1* | 5/2015 | Christianson | C08F 10/00 526/131 |
| 2016/0303551 A1* | 10/2016 | Zoricak | B01J 31/143 |

FOREIGN PATENT DOCUMENTS

| | | |
|---|---|---|
| CN | 1227257 | 11/2005 |
| CN | 1741849 | 3/2006 |
| EP | 0722922 | 7/1996 |
| JP | 49-134603 | 12/1974 |
| KR | 10-0435513 | 6/2004 |
| KR | 10-0479386 | 7/2005 |
| KR | 10-2014-0103112 | 8/2014 |
| KR | 10-2015-0058018 | 5/2015 |
| KR | 10-2015-0058049 | 5/2015 |
| WO | 2000-058319 | 10/2000 |

OTHER PUBLICATIONS

KIPO, Search Report & Written Opinion of Application No. PCT/KR2016/010526, dated Jan. 12, 2017.
Takashi Monoi et al., "Silica-supported Cr[N(SiMe3)2]3/isobutylalumoxane catalyst for selective ethylene trimerization", Journal of Molecular Catalysis A: Chemical, 187(Dec. 31, 2002), 135-141.

* cited by examiner

*Primary Examiner* — Ali Z Fadhel
(74) *Attorney, Agent, or Firm* — Lex IP Meister, PLLC

(57) ABSTRACT

The present invention relates to a catalyst system for olefin oligomerization, and a method for oligomerizing olefins using the same. The catalyst system for olefin oligomerization according to the present invention exhibits high selectivity to 1-hexene and 1-octene while having excellent catalytic activity, thereby enabling more efficient preparation of alpha-olefins.

7 Claims, No Drawings

CATALYST SYSTEM FOR OLEFIN OLIGOMERIZATION AND METHOD FOR OLIGOMERIZING OLEFINS USING THE SAME

CROSS-REFERENCE TO RELATED APPLICATION(S)

This application claims priority to and the benefit of Korean Patent Application No. 10-2015-0134727 filed on Sep. 23, 2015 with the Korean Intellectual Property Office, the disclosure of which is incorporated herein by reference in its entirety.

TECHNICAL FIELD

The present invention relates to a catalyst system for olefin oligomerization, and a method for oligomerizing olefins using the same.

BACKGROUND ART

Linear alpha-olefins are widely used commercially as important materials used for comonomers, detergents, lubricants, plasticizers, etc., and in particular, 1-hexene and 1-octene are widely used as comonomers for controlling the density of polyethylene during the preparation of linear low-density polyethylene (LLDPE).

In addition, since alpha-olefins have various different application fields or market sizes according to the kind, a technology of selectively producing a specific olefin is commercially very important, and recently, many studies have progressed on chromium catalyst technology for preparing 1-hexene or 1-octene with high selectivity through selective ethylene oligomerization.

Specifically, U.S. Pat. No. 7,361,623 discloses a catalyst system for the production of 1-hexene and 1-octene using chromium as a central metal, but this catalyst system does not consistently maintain the reaction activity depending on the reaction time, and the reaction rate tends to greatly decrease.

In addition, Korean Patent No. 10-0435513 discloses a catalyst system for the production of 1-hexene using chromium as a central metal, but this catalyst system exhibits performance of the catalyst under the conditions of high temperature and high pressure, and thus there is a limit in terms of energy consumption with this type of catalyst.

Accordingly, there has been a continuing demand for multimerization reaction activity and high selectivity which are consistently maintained during the reaction when preparing alpha-olefins such as 1-octene or 1-hexene.

PRIOR ART LITERATURE

Patent Literature (Patent Literature 1) U.S. Pat. No. 7,361,623
(Patent Literature 2) Korean Patent No. 10-0435513

DETAILED DESCRIPTION OF THE INVENTION

Technical Problem

It is an object of the present invention to provide a catalyst system for olefin oligomerization that can oligomerize olefins with high catalytic activity and selectivity, and a method for oligomerizing olefins using the same.

Technical Solution

The present invention provides a catalyst system for olefin oligomerization including: a ligand compound represented by Chemical Formula 1 below; a transition metal source; and a cocatalyst.

The present invention also provides a method for oligomerizing olefins including a step of subjecting an olefin to a multimerization reaction in the presence of the catalyst system for olefin oligomerization.

A catalyst system for olefin oligomerization and a method for oligomerizing olefins according to a specific embodiment of the invention will be described in more detail below.

As used herein, the term "olefin oligomerization" means polymerization of a small number of olefins.

Depending on the number of olefins to be polymerized, it is referred to as trimerization or tetramerization, and is collectively referred to as multimerization.

In particular, in the present invention, it refers to selectively preparing 1-hexene and 1-octene from ethylene.

According to one embodiment of the invention, a catalyst system for olefin oligomerization is provided, including: a ligand compound represented by Chemical Formula 1 below; a transition metal source; and a cocatalyst.

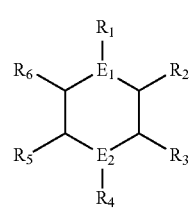

[Chemical Formula 1]

in the above Chemical Formula 1, $E_1$ and $E_2$ are each independently an element selected from the group consisting of boron (B), nitrogen (N), oxygen (O), silicon (Si), phosphorus (P), and sulfur (S), and $R_1$ to $R_6$ each independently represent hydrogen, an alkyl group having 1 to 20 carbon atoms, a cycloalkyl group having 3 to 20 carbon atoms, an alkylsilyl group having 1 to 20 carbon atoms, a haloalkyl group having 1 to 20 carbon atoms, an aryl group having 6 to 40 carbon atoms, an arylalkyl group having 7 to 20 carbon atoms, an arylsilyl group having 6 to 20 carbon atoms, an alkylaryl group having 7 to 20 carbon atoms, an alkoxy group having 1 to 20 carbon atoms, an alkylsiloxy group having 1 to 20 carbon atoms, an aryloxy group having 6 to 20 carbon atoms, a halogen group, or an amino group.

The present inventors conducted intensive studies and experiments, and found that, since a catalyst system for olefin oligomerization including a ligand compound having the above specific structure, a transition metal source, and a cocatalyst can easily control an electronic and stereoscopic environment around the transition metal by appropriately controlling the substituents that are introduced into the ligand compound, it is possible to oligomerize olefins with high catalytic activity and selectivity, thereby completing the invention.

In particular, the ligand compound is a hexagonal ring compound and includes a heteroelement such as boron (B), nitrogen (N), oxygen (O), silicon (Si), phosphorus (P), and sulfur (S). However, due to these structural features, the ligand compound can be applied to oligomerization catalyst systems of olefins to exhibit high oligomerization reaction activity, and particularly exhibit high selectivity to 1-hexene and 1-octene.

This is presumed to be due to the interaction between each adjacent chromium active site.

Meanwhile, in the ligand compound represented by Chemical Formula 1, at least one of $E_1$ and $E_2$ may be nitrogen (N) or oxygen (O).

In the ligand compound, particularly when nitrogen or oxygen rich in electrons is introduced at the position of $E_1$ or $E_2$, the stability when the central metal becomes a cation can be improved.

Consequently, the catalyst system for olefin oligomerization containing such a ligand compound can exhibit high activity in an oligomerization reaction.

In Chemical Formula 1, $R_1$ to $R_6$ may be hydrogen, an alkyl group having 1 to 20 carbon atoms, a cycloalkyl group having 3 to 20 carbon atoms, an alkylsilyl group having 1 to 20 carbon atoms, a haloalkyl group having 1 to 20 carbon atoms, an aryl group having 6 to 40 carbon atoms, an arylalkyl group having 7 to 20 carbon atoms, an arylsilyl group having 6 to 20 carbon atoms, an alkylaryl group having 7 to 20 carbon atoms, an alkoxy group having 1 to 20 carbon atoms, an alkylsiloxy group having 1 to 20 carbon atoms, an aryloxy group having 6 to 20 carbon atoms, a halogen group, or an amino group. The aryl group may be an aromatic hydrocarbon functional group such as phenyl, biphenyl, triphenyl, triphenylene, naphthylenyl, anthracenyl, phenalenyl, phenanthrenyl, fluorenyl, pyrenyl, chrycenyl, perylenyl, azulenyl, and the like, and an aromatic heterocyclic functional group such as dibenzothiophenyl, dibenzofuranyl, dibenzoselenophenyl, furanyl, thiophenyl, benzofuranyl, benzothiophenyl, benzoselenophenyl, carbazolyl, indolocarbazolyl, pyridylindolinin, pyrrolodipyridinyl, pyrazolyl, imidazolyl, triazolyl, oxazolyl, thiazolyl, oxadiazolyl, oxatriazolyl, dioxazolyl, thiadiazolyl, pyridyl, pyridazynyl, pyrimidyl, pyrazinyl, triazinyl, oxazinyl, oxathiazinyl, oxadiazinyl, indolinin, benzimidazolyl, indazolyl, indoxazinyl, benzoxazolyl, benzisoxazolyl, benzothiazolyl, quinolinin, isoquinolinyl, cinnolinyl, quinazolyl, quinoxalinin, naphthyridyl, phthalazinyl, phtheridinyl, xanthanyl, acridyl, phenazinyl, phenothiazinyl, phenoxazinyl, benzofuropyridyl, furodipyridyl, benzothienopyridyl, thienodipyridyl, benzoselenophenopyridyl, selenophenodipyridyl, and the like.

At least one of $R_1$ and $R_4$ in Chemical Formula 1 is more preferably an alkyl group, a cycloalkyl group, or an aryl group having 1 to 20 carbon atoms, from the viewpoint of the stabilization of the central metal.

The ligand compound may include piperazine substituted with one or more functional groups selected from the group consisting of an alkyl group having 1 to 5 carbon atoms and a cycloalkyl group having 4 to 10 carbon atoms.

As piperazine substituted with one or more functional groups selected from the group consisting of an alkyl group having 1 to 5 carbon atoms and a cycloalkyl group having 4 to 10 carbon atoms is used as the ligand compound, the catalyst system for olefin oligomerization of the above embodiment can realize improved activity while having more stable electron distribution characteristics, and the catalyst system can secure a higher reaction yield and a higher reaction rate in the olefin oligomerization reaction.

Specific examples of the ligand compounds are as follows.

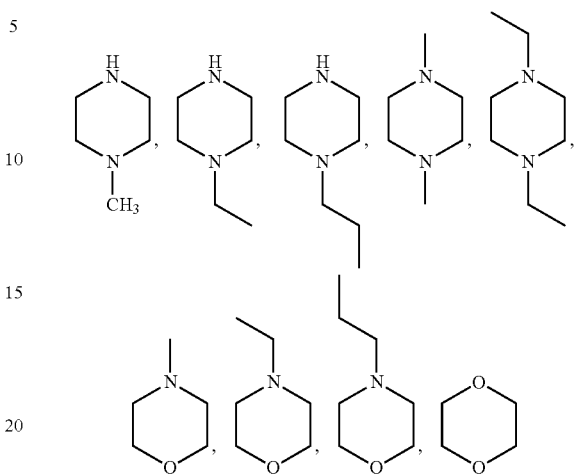

In addition, the transition metal source of the catalyst system for olefin oligomerization of one embodiment serves as a main catalyst, and it is preferable to use a compound containing chromium(III) or chromium(II) because it can increase the reaction activity.

As the above chromium(III) compound, chromium carboxylate, chromium naphthenate, chromium halide, chromium dionate, and the like can be used. More specific examples thereof include chromium(III) 2,2,6,6-tetramethylheptanedionate, chromium(III) 2-ethylhexanoate, chromium(III) tris(2-ethylhexanoate), chromium(III) naphthenate $[Cr(NP)_3]$, chromium(III) chloride, chromium(III) bromide, chromium(III) fluoride, chromium(III) acetylacetonate, chromium(III) acetate, chromium(III) butyrate, chromium (III) neopentanoate, chromium(III) laurate, chromium(III) stearate, chromium(III) oxalate, and the like.

Further, specific examples of the chromium(II) compound include chromium(II) bromide, chromium(II) fluoride, chromium(II) chloride, chromium(II) bis(2-ethylhexanoate), chromium(II) acetate, chromium(II) butyrate, chromium(II) neopentanoate, chromium(II) laurate, chromium(II) stearate, chromium(II) oxalate, and the like.

Meanwhile, the transition metal source may be in a state of being dissolved in a hydrocarbon solvent.

The hydrocarbon solvent is an inert solvent that does not react with a transition metal source, a cocatalyst and the like, and examples thereof include benzene, benzene, toluene, heptane, cyclohexane, methylcyclohexane, methylcyclopentane, hexane, pentane, butane, isobutane, and like, but are not limited thereto.

In the catalyst system for olefin oligomerization of the above embodiment, chromium(III) 2-ethylhexanoate is used as the transition metal source, and it is preferable that it is dissolved in an anhydrous toluene or anhydrous cyclohexane solvent before use, from the viewpoint of improving the catalytic activity due to the difference in solubility of the catalyst.

Further, the cocatalyst of the catalyst system for olefin oligomerization of one embodiment is a metal alkyl compound, and is not particularly limited as long as it can be typically used when multimerizing olefins in the presence of a transition metal compound catalyst.

Specifically, as the metal alkyl compound, an alkyl aluminum compound, an alkyl boron compound, an alkyl magnesium compound, an alkyl zinc compound, an alkyl lithium compound, or the like can be used.

However, in order to exhibit high selectivity and activity in the olefin oligomerization reaction, it is preferable to use an alkyl aluminum compound as the cocatalyst compound. Specific examples of such alkyl aluminum compound include triethyl aluminum, tripropyl aluminum, tributyl aluminum, diethyl aluminum chloride, diethyl aluminum bromide, diethyl aluminum ethoxide, diethyl aluminum phenoxide, ethyl aluminum dichloride, ethyl aluminum sesquichloride, and the like.

As a cocatalyst of the catalyst system for the olefin oligomerization according to one embodiment, preferably, triethylaluminum, ethylaluminum dichloride, and ethylaluminum sesquichloride may be mixed and used. In this case, water can be effectively removed, and the catalytic activity including electron donor atoms is improved, which is preferable.

In addition, in order to increase the selectivity for the linear alpha olefin and increase the multimerization reaction activity, the catalyst system for the olefin oligomerization may have a molar ratio of the ligand compound to the transition metal source to the cocatalyst in the range of about 0.5:1:1 to about 10:1:10,000, and preferably about 0.5:1:100 to about 5:1:3000.

However, the present invention is not limited thereto.

Meanwhile, according to another embodiment of the present invention, a method for producing an olefin oligomer can be provided, including a step of subjecting an olefin to a multimerization reaction in the presence of the catalyst system for olefin oligomerization.

Using the catalyst system for olefin oligomerization of the above embodiment can provide a method for oligomerizing olefins having improved reaction activity and selectivity.

At this time, the olefin is preferably ethylene.

The olefin oligomerization according to the present invention may be conducted by a homogeneous liquid phase reaction, a slurry reaction wherein a catalyst system is partially or completely dissolved, a two-phase liquid/liquid reaction, or a bulk phase reaction or a gas phase reaction wherein an olefin product acts as a main medium, in the absence or presence of an inert solvent, using the catalyst system for olefin oligomerization and a common device and contact technology, and the homogeneous liquid phase reaction is preferable.

The olefin oligomerization reaction can be carried out in any inert solvent that does not react with a catalyst compound and an activator.

Suitable inert solvents include benzene, toluene, xylene, cumene, heptane, cyclohexane, methylcyclohexane, methylcyclopentane, hexane, pentane, butane, isobutane, etc., but are not limited thereto.

In this case, the solvent can be used by treating with a small amount of alkylaluminum and thereby removing a small amount of water or air acting as a catalyst poison.

The olefin oligomerization reaction may be carried out at a temperature of about 0° C. to about 250° C., preferably about 20° C. to about 200° C., and more preferably about 40° C. to about 130° C.

An excessively low reaction temperature can produce an excessive amount of undesirable insoluble products such as polymers, and an excessively high temperature can induce decomposition of the catalyst system. Therefore, it is preferable that the reaction proceeds within the above temperature range.

Further, the olefin oligomerization reaction may be carried out at a pressure from about 1 bar to about 200 bar, preferably at a pressure from about 10 bar to about 150 bar.

An excessively low reaction pressure can lead to low catalytic activity, which is undesirable.

In the process of preparing the olefin oligomer, hydrogen may be added to the reactor at about 0.01 to 50 bar, and preferably at about 0.5 to 10 bar, in order to facilitate the reaction or increase the activity of the catalyst system.

Advantageous Effects

The use of a catalyst system including a ligand compound according to the present invention enables oligomerization of ethylene with high catalytic activity and selectivity compared to existing catalyst systems, and the stability of the catalyst is excellent and thus a more stable polymerization reaction is possible.

DETAILED DESCRIPTION OF THE EMBODIMENTS

The present invention will be described in more detail with reference to the following examples. However, these examples are given for illustrative purposes only, and the scope of the invention is not intended to be limited thereto.

Examples and Comparative Example: Preparation of a Catalyst System for Olefin Oligomerization Example 1

30 mL (21.3 mmol) of chromium(III) 2-ethylhexanoate was dissolved in anhydrous toluene and 63.8 mmol of 1-methylpiperazine ligand was added thereto.

In a separate vessel, 85.1 mmol of ethylaluminum dichloride and 319 mmol of triethylaluminum were mixed together.

Then, the mixed solution of ethylaluminum dichloride and triethylaluminum was slowly added to the chromium compound/ligand solution.

Subsequently, the dark yellowish brown solution was stirred for 5 minutes and the solvent was removed under vacuum.

The remaining oily liquid was diluted with 150 mL of cyclohexane and the solution was filtered to remove a black precipitate from the filtrate containing the catalyst system, and this was diluted with toluene to have a volume of 250 mL to prepare a catalyst system for olefin oligomerization.

Example 2

A catalyst system for olefin oligomerization was prepared in the same manner as in Example 1, except that 1000 ml of anhydrous cyclohexane was used instead of anhydrous toluene.

Example 3

A catalyst system for olefin oligomerization was prepared in the same manner as in Example 1, except that ethyl aluminum sesquichloride (85.1 mmol) was used instead of ethyl aluminum dichloride.

Comparative Example 1

A catalyst system for olefin oligomerization was prepared in the same manner as in Example 1, except that 2,5-dimethylpyrrole (63.8 mmol) was used instead of the 1-methylpiperazine ligand.

Experimental Example: Olefin Oligomerization

A 2 L stainless steel reactor was charged with nitrogen to which 1 L of reaction solvent was added, 3 mL of triethylaluminum was added, ethylene was charged at 10 bar, and the temperature was raised to 90° C.

Then, the catalyst solution prepared in Examples 1 to 3 or Comparative Example 1 was added to a reactor, charged with ethylene at 35 bar, and then stirred at a stirring speed of 500 rpm.

After one hour, feeding of ethylene to the reactor was stopped, the stirring was stopped, and the reaction was stopped. The reactor was cooled to below 10° C.

After excess ethylene was discharged from the reactor, ethanol mixed with 10 vol % hydrochloric acid was injected into the liquid contained in the reactor.

A small amount of the organic layer sample was passed over silica gel, dried, and then analyzed by GC-FID.

The remaining organic layer was filtered to separate the solid wax/polymer product.

These solid products were dried in an oven at 80° C. for 8 hours to give polyethylene and then weighed.

The results of the production of 1-hexene and 1-octene using the catalysts prepared in the respective examples and comparative example are shown in Table 1 below.

TABLE 1

| Catalyst | Reaction solvent | 1-hexene (wt %) | 1-octene (wt %) | Activity | PE (g) |
|---|---|---|---|---|---|
| xample 1 | Cyclohexane | 21.2 | 76.0 | 5.2 | 2.8 |
| Example 1 | Toluene | 17.9 | 81.0 | 6.1 | 0.8 |
| Example 2 | Cyclohexane | 20.4 | 77.5 | 4.5 | 2.1 |
| Example 2 | Toluene | 25.9 | 72.9 | 3.2 | 1.2 |
| Example 3 | Cyclohexane | 19.3 | 78.8 | 5.6 | 1.9 |
| Example 3 | Toluene | 22.5 | 77.3 | 5.9 | 1.2 |
| Comparative Example 1 | Cyclohexane | 92.3 | 5.1 | 3.2 | 2.6 |

* Catalytic activity unit: (Kg of Product/mmol of Cat)

As shown in Table 1, it was confirmed that the experimental examples using the catalyst systems of the examples produce a low amount of polyethylene (byproduct) while exhibiting high catalytic activity.

In addition, in the experimental examples using the catalyst systems of the examples, the selectivity to 1-octene was 70 wt % or more, which confirms that the 1-octene selectivity was significantly improved as compared with the case of using the catalyst system of the comparative example.

The invention claimed is:

1. A catalyst system for olefin oligomerization comprising:
   a ligand compound;
   a transition metal source; and
   a cocatalyst,
   wherein the ligand compound is selected from the group consisting of:

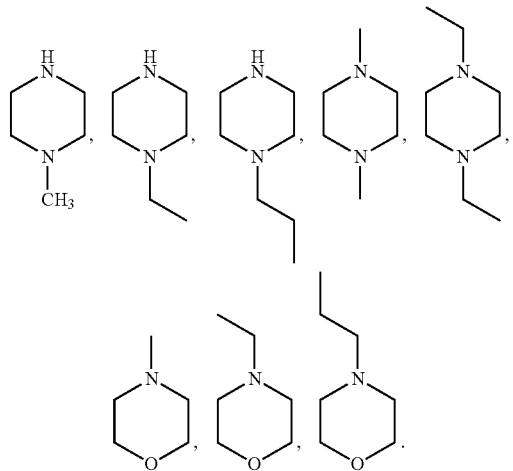

2. The catalyst system for olefin oligomerization of claim 1, wherein the transition metal source includes one or more compounds selected from the group consisting of chromium (III) 2,2,6,6-tetramethylheptanedionate, chromium(III) 2-ethylhexanoate, chromium(III) tris(2-ethylhexanoate), chromium(III) naphthenate [Cr(NP)$_3$], chromium(III) chloride, chromium(III) bromide, chromium(III) fluoride, chromium(III) acetylacetonate, chromium(III) acetate, chromium(III) butyrate, chromium(III) neopentanoate, chromium (III) laurate, chromium(III) stearate, chromium(III) oxalate, chromium bromide, chromium fluoride, chromium chloride, chromium(II) bis(2-ethylhexanoate), chromium(II) acetate, chromium(II) butyrate, chromium(II) neopentanoate, chromium(II) laurate, chromium(II) stearate, and chromium(II) oxalate.

3. The catalyst system for olefin oligomerization of claim 1, wherein the cocatalyst is one or more alkyl aluminum compounds selected from the group consisting of triethyl aluminum, tripropyl aluminum, tributyl aluminum, diethyl aluminum chloride, diethyl aluminum bromide, diethyl aluminum ethoxide, diethyl aluminum phenoxide, ethyl aluminum dichloride, and ethyl aluminum sesquichloride.

4. The catalyst system for olefin oligomerization of claim 1, wherein the molar ratio of the ligand compound to the transition metal source to the cocatalyst is in the range of 0.5:1:1 to 10:1:10,000.

5. A method for oligomerizing olefins comprising a step of subjecting an olefin to a multimerization reaction in the presence of the catalyst system for olefin oligomerization of claim 1.

6. The method for oligomerizing of claim 5, wherein the multimerization reaction temperature is 0 to 250° C.

7. The method for oligomerizing of claim 5, wherein the multimerization reaction pressure is 1 to 200 bar.

* * * * *